(12) United States Patent
Merschon et al.

(10) Patent No.: US 11,020,165 B2
(45) Date of Patent: Jun. 1, 2021

(54) TOUCH FREE OPERATION OF ABLATOR WORKSTATION BY USE OF DEPTH SENSORS

(71) Applicant: BIOSENSE WEBSTER (ISRAEL) LTD., Yokneam (IL)

(72) Inventors: Asaf Merschon, Maor (IL); Assaf Govari, Haifa (IL); Andres Claudio Altmann, Haifa (IL); Yitzhack Schwartz, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 16/869,360

(22) Filed: May 7, 2020

(65) Prior Publication Data

US 2020/0261143 A1 Aug. 20, 2020

Related U.S. Application Data

(63) Continuation of application No. 15/995,007, filed on May 31, 2018, now Pat. No. 10,653,472, which is a
(Continued)

(51) Int. Cl.
*G06F 3/033* (2013.01)
*A61B 18/12* (2006.01)
(Continued)

(52) U.S. Cl.
CPC .......... *A61B 18/1206* (2013.01); *G06F 3/017* (2013.01); *A61B 34/25* (2016.02);
(Continued)

(58) Field of Classification Search
None
See application file for complete search history.

(56) References Cited

U.S. PATENT DOCUMENTS 6,243,683 B1 6/2001 Peters
6,368,269 B1 4/2002 Lane
(Continued)

FOREIGN PATENT DOCUMENTS

CN 101119680 A 2/2008
JP 2000-0347692 A 6/1999
(Continued)

OTHER PUBLICATIONS

English Translation of Japanese Notification of Reasons for Refusal dated Aug. 30, 2016 from related Japanese Patent Application No. 2013-002425, 5 pages.
(Continued)

*Primary Examiner* — Carl Adams
(74) *Attorney, Agent, or Firm* — Lewis Roca Rothgerber Christie LLP

(57) ABSTRACT

An inventive system and method for touch free operation of an ablation workstation is presented. The system can comprise a depth sensor for detecting a movement, motion software to receive the detected movement from the depth sensor, deduce a gesture based on the detected movement, and filter the gesture to accept an applicable gesture, and client software to receive the applicable gesture at a client computer in an ablation workstation for performing a task in accordance with client logic based on the applicable gesture. The system can also comprise hardware for making the detected movement an applicable gesture. The system can also comprise voice recognition providing voice input for enabling the client to perform the task based on the voice input in conjunction with the applicable gesture. The applicable gesture can be a movement authorized using facial recognition.

16 Claims, 3 Drawing Sheets

Related U.S. Application Data continuation of application No. 15/875,988, filed on Jan. 19, 2018, now Pat. No. 10,052,147, which is a continuation of application No. 13/347,987, filed on Jan. 11, 2012, now Pat. No. 9,931,154.

(51) Int. Cl.
| | | |
|---|---|---|
| *G06F 3/01* | (2006.01) | |
| *A61B 34/00* | (2016.01) | |
| *A61B 17/00* | (2006.01) | |
| *A61B 18/00* | (2006.01) | |

(52) U.S. Cl.
CPC ........... *A61B 2017/00203* (2013.01); *A61B 2017/00207* (2013.01); *A61B 2017/00216* (2013.01); *A61B 2017/00221* (2013.01); *A61B 2017/00973* (2013.01); *A61B 2018/00577* (2013.01); *A61B 2018/00988* (2013.01)

(56) References Cited

U.S. PATENT DOCUMENTS

| | | |
|---|---|---|
| 7,835,498 B2 | 11/2010 | Bonfiglio et al. |
| 2001/0039415 A1* | 11/2001 | Francischelli ......... A61B 5/411 606/27 |
| 2004/0036574 A1 | 2/2004 | Bostrom |
| 2006/0247822 A1 | 11/2006 | Nishizawa |
| 2008/0273755 A1 | 11/2008 | Hildreth |
| 2008/0319507 A1 | 12/2008 | Myers |
| 2009/0079813 A1 | 3/2009 | Hildreth |
| 2009/0228841 A1 | 9/2009 | Hildreth |
| 2009/0281809 A1 | 11/2009 | Reuss |
| 2010/0013764 A1 | 1/2010 | Gu et al. |
| 2010/0053187 A1 | 3/2010 | Arrasvuori |
| 2010/0228119 A1 | 9/2010 | Brennan et al. |
| 2010/0231509 A1* | 9/2010 | Boillot .................. A61B 34/25 345/156 |
| 2010/0277489 A1 | 11/2010 | Geisner et al. |
| 2010/0280363 A1 | 11/2010 | Skarda et al. |
| 2011/0007142 A1 | 1/2011 | Perez et al. |
| 2011/0118877 A1* | 5/2011 | Hwang .................. B25J 13/00 700/264 |
| 2011/0254846 A1 | 10/2011 | Lee |
| 2011/0313768 A1 | 12/2011 | Klein et al. |
| 2011/0320949 A1* | 12/2011 | Ohki .................... G06F 40/177 715/727 |
| 2012/0089392 A1 | 4/2012 | Larco et al. |
| 2012/0093360 A1 | 4/2012 | Subramanian |
| 2012/0191993 A1* | 7/2012 | Drader .................. G09G 5/006 713/320 |
| 2014/0007225 A1 | 1/2014 | Gay |

FOREIGN PATENT DOCUMENTS

| | | |
|---|---|---|
| JP | 2008-529707 A | 8/2008 |
| JP | 2011-517357 A | 6/2011 |
| JP | 2011-232964 A | 11/2011 |
| WO | WO 07/127338 A2 | 11/2007 |
| WO | WO 09/137688 A2 | 11/2009 |
| WO | WO 11/123669 A1 | 10/2011 |

OTHER PUBLICATIONS

English Translation of Japanese Notification of Reasons for Refusal dated Aug. 30, 2016 from corresponding Japanese Patent Application No. 2013-002419, 5 pages.
English Translation of Chinese First Office Action dated Oct. 10, 2016 from related Chinese Patent Application No. 201310011537.3, 17 pages.
Chinese First Office Action dated Sep. 20, 2016 from corresponding Chinese Patent Application No. 201310009173.5., English translation only, 9 pages.
Australian Exam Report dated Sep. 17, 2014 for corresponding Australian Application No. 2013200053.
Australian Exam Report dated Sep. 17, 2014 for related Australian Application No. 2013200054.
Australian Exam Report dated Sep. 7, 2015 for related Australian Application No. 2013200054.
Australian Exam Report dated Oct. 12, 2015 for related Australian Application No. 2013200054.
Australian Exam Report dated Nov. 2, 2015 for related Australian Application No. 2013200054.
European Search Report dated Apr. 9, 2013 for related European Patent Application No. 13150838.
European Search Report dated Apr. 13, 2016 for related European Patent Application No. 13150838.4, 9 pages.
European Examination Report dated Sep. 8, 2014 for related European Patent Application No. 13150838.4.
Wachs, Juan P. et al., "A Gesture-based Too for Sterile Browsing of Radiology Images", Journal of the American Medical Informatics Association, vol. 15, No. 3, May/Jun. 2008, pp. 321-323.
Fried, Craig et al., "A Real-Time Gesture Interface for Hands-Free Control of Electronic Medical Records", AMIA 2006 Symposium Proceedings, 2006, p. 920.
Wachs, Juan et al., "Real-Time Hand Gesture Interface for Browsing Medical Images", IC-MED, vol. 1, Mo. 3, Issue 1, pp. 175-185.
"Hand Gesture Interface for Medical Visualization Applications (Gestix)", http://),vww.movesinstitutes.org/jpwachs/gestix/gesture.html, printed Jun. 22, 2011.
EPO European Search Report dated Nov. 20, 2019 for EP Application No. 19193179.9, 12 pages.

\* cited by examiner

TOUCH FREE OPERATION OF ABLATOR WORKSTATION BY USE OF DEPTH SENSORS

CROSS-REFERENCE TO RELATED APPLICATIONS

This application is a continuation of U.S. patent application Ser. No. 15/995,007, filed May 31, 2018, now U.S. Pat. No. 10,653,472, which is a continuation of U.S. patent application Ser. No. 15/875,988, filed Jan. 19, 2018, now U.S. Pat. No. 10,052,147, which is a continuation of U.S. patent application Ser. No. 13/347,987, filed Jan. 11, 2012, now U.S. Pat. No. 9,931,154, the entire contents all of which are incorporated herein by reference.

This application is related to commonly-owned, U.S. patent application Ser. No. 13/347,943 filed on Jan. 11, 2012, now U.S. Pat. No. 9,625,993, entitled TOUCH FREE OPERATION OF DEVICES BY USE OF DEPTH SENSORS, the entire contents and disclosure of which are expressly incorporated by reference herein as if fully set forth herein.

FIELD OF THE INVENTION

The present invention relates generally to touch free operation of operating room devices by using depth sensors and, in some situations, voice recognition.

BACKGROUND OF THE INVENTION

In an operating room, the physician needs to stay sterile; hence he or she cannot physically access a computer for assistance during surgery. Accordingly, any task the physician wants to perform using computer applications on operating room devices, such as an ablator workstation, must actually be performed by another. There is a need for the physician to be able to operate these devices without physically touching the device or its accessories, e.g., its keyboard, screen, mouse, etc.

SUMMARY OF THE INVENTION

An inventive system and method for touch free operation of an ablator workstation is presented. The system comprises a depth sensor for detecting a movement, a motion software module operable to receive the detected movement from the depth sensor, deduce a gesture based on the detected movement, and filter the gesture to accept an applicable gesture, and a client software module operable to receive the applicable gesture at a client computer in or associated with the ablator workstation for performing a task in accordance with client logic based on the applicable gesture.

In one aspect, the task is one of changing power settings of one or more electrodes, changing maximum allowed temperature for one or more electrodes, changing ablation mode between unipolar and bipolar, selecting and deselecting electrodes for ablation. In one aspect, the movement is at least one of a head motion, a hand motion and a body motion and the gesture is further deduced based on a short history. In one aspect, the system further comprises hardware for making the detected movement an applicable gesture. In one aspect, the applicable gesture is one or more of the detected movement performed by a user determined to be authorized using facial recognition, and a recognized gesture in accordance with the client logic. In one aspect, filtering of the gesture is performed by determining whether the gesture is authorized and valid. In one aspect the system further comprises a client communication module for receiving the application gesture at the client computer. In one aspect, the system further comprises voice recognition providing voice input for enabling the client to perform the task based on the voice input in conjunction with the applicable gesture.

An inventive method for touch free operation of an ablator workstation comprises detecting a movement using a depth sensor, deducing, using a CPU, a gesture based on the detected movement, filtering the gesture to accept an applicable gesture, receiving the applicable gesture at a client in the ablator workstation, and performing a task in accordance with client logic based on the applicable gesture.

A computer readable storage medium storing a program of instructions executable by a machine to perform one or more methods described herein also may be provided.

BRIEF DESCRIPTION OF THE DRAWINGS

The present invention will be more fully understood from the following detailed description of the embodiments thereof, taken together with the drawings. Further features as well as the structure and operation of various embodiments are described in detail below with reference to the accompanying drawings. In the drawings, like reference numbers indicate identical or functionally similar elements.

DETAILED DESCRIPTION

An inventive technique for touch free operation of an ablator workstation is presented. In accordance with this novel technology, a person can perform the ablator workstation functions without touching any computer apparatus, e.g., a monitor, a keyboard, a mouse, etc.

Figure 1:
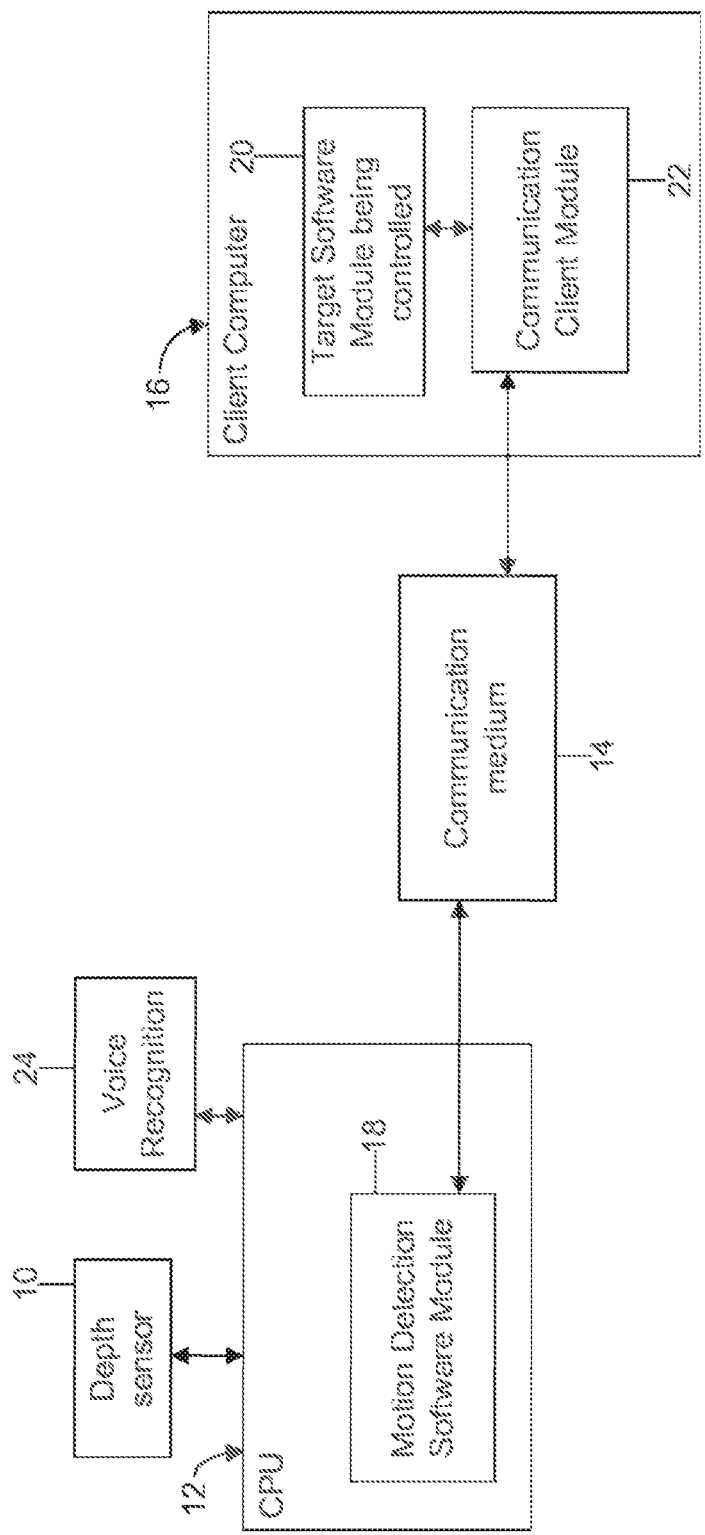
FIG. 1 is a block diagram of an embodiment of the inventive system.

As shown in FIG. 1, the system in one embodiment comprises various components including a depth sensor 10, a computer or CPU 12, a communication medium 14 and a client computer 16 which is part of the ablator workstation. A Motion Detection Software Module 18 can reside in the CPU 12. The client computer 16 can control a Target Software Module 20. A Communication Client Module 22 can reside in the client computer 16. In one embodiment, the system can also include voice recognition, such as a microphone or a microphone array 28.

The depth sensor 10 typically includes a depth-aware camera that not only records images but also records depth, allowing 3D representation of the recorded images. As is known to one skilled in the art, a depth sensor is connected to a computer which uses the depth map from the sensor to deduce motion, e.g., hand gestures, poses and positions of a user. In a medical setting, the user can be the system operator, generally a physician. In one embodiment of the present invention, the depth sensor tracks movements of the head as well as the hands. In another embodiment, the depth sensor tracks not only the hands and head but also the overall body location, such as movement toward and/or away from the computer screen or monitor. In one embodiment, the depth sensor 10 can be implemented using modules or middleware such as Microsoft® Kinect, ASUS® Xtion PRO, or ASUS® Xtion PRO LIVE. More than one depth sensor can be used in parallel to extend occlusion handling, field of view and accuracy. Any sensor, such as a camera which can provide a depth map with sufficient detail in real time, may be fitted for use with the inventive system. The depth sensor obtains location information and forwards this information to CPU 12 for processing as discussed below. As is known to one skilled in the art, software and a driver provided by the depth sensor 10 can be used to obtain this location information.

The Motion Detection Software Module or Motion Software 18 in the CPU 12 obtains the location information, such as locations of the operator's relevant body parts, e.g., hand, head, feet, etc., a few times a second, from the depth sensor 10. Each received motion and/or body location is tracked and saved to a short history of movements file or data set.

The motion software can include software that uses the data detected as movements of the body parts from the motion software 18 along with the short history of movements data to deduce more complex movements and process the data into significant gestures, such as a motion forward, a circular motion of the hand, or a nod with the head. For example, linear movements and/or circular movements of the hand are detected and parameters are calculated to quantify these movements. The motion software associates particular attributes, such as the extent of the movement, the time it was captured, its speed and/or duration, etc., with each gesture.

The system can be associated with a specific user by using body tracking, that is, starting from an initial configuration, tracking a user's individual movements, and ensuring that only motions by that specific user are responded to. For example, locations of the body and movements are tracked and so long as the differences from locations in the previous frame are small enough, the movements are assumed to be the same person. The system can also be associated with a specific user by employing face detection and/or recognition with the camera in the depth sensor. The system can use face detection and/or recognition to verify that the body is the one associated with the recognized face in each state or position. These techniques can be combined, for example, using body tracking while the movements are small and, whenever there is an uncertainty, using face detection and/or recognition to find the correct user, and then continue as before.

The Motion Detection Software Module 18 can also include a filter that can decide which motions or movements to accept and which need to be ignored or filtered out as not applicable, e.g., invalid and/or unauthorized. An invalid, e.g., irrelevant, motion can be a motion that is not acceptable to the Motion Detection Software Module 18. For example, if a motion is too small or slow to filter uncontrollable natural movements of the user, then this motion would be invalid or irrelevant. An unauthorized motion is a motion that is not performed by the proper user and/or not performed in accordance with predetermined conditions. For example, for safety and/or security, certain motions can require physical input and/or interaction with a corresponding hardware device, such as the pressing of a foot pedal during a particular hand motion and/or at a given time during the procedure. In one embodiment when multiple cameras are used and one camera has a view of the physician's full body, it could be determined whether the specific physician provided the appropriate physical input. This security measure, e.g., requiring physical input in addition to detected motions, trusts that the people in the room are not trying to tamper with the system; instead, the security measure provides extra security to prevent critical functions from happening unintentionally, in case the physician/user made some gesture by mistake.

Connecting a hardware device to the system can prevent unwanted actions by the system, as indicated above. This can be critical in medical software. The hardware device (not shown), e.g., a foot pedal, could be connected to the client computer 16 and/or the ablator workstation which it is responsible for receiving and interpreting the device actions, e.g., foot pedal presses, etc., and using these actions for the internal logic of the client. The hardware device could also be connected to the CPU 12 doing the motion detection and its software in which case the device state could be sent with the motions detected and/or some motions could be filtered according to the state of the device.

The motions not filtered out are sent through the communication medium 14 to the communications client module 20 at the client computer 16. The communication medium 14 can be a serial, local area network (LAN), wireless LAN (WLAN), Bluetooth, wireless, etc.

The client computer 16 receives the interpreted motions, e.g., gesture. The Target Software Module 20 determines if the received motion is valid. An invalid motion can be a motion that is not defined within the Target Software Module 20. For example, when one client software module is active, then a motion toward the screen can be defined to change the mode to unipolar, but if another client were active, this motion toward the screen may not be defined so that this motion would be inappropriate or irrelevant. In addition, an invalid motion can be one that is not permitted unless certain preconditions are met. For example, when a hardware device is connected to the client computer, a motion can be permitted or valid only when it is performed in conjunction with an action of the hardware device; for example, a wave motion may only be valid when it is performed while a foot pedal of a hardware device is pressed.

Client logic, e.g., Target Software Module 20, determines how to respond to each recognized, e.g., valid, gesture. The Target Software Module 20 is associated with the ablator workstation and the client logic may be able to perform tasks such as changing the power settings, selecting and deselecting electrodes, changing the maximum allowed temperature per electrode, etc. Accordingly, the client software may determine, using its logic, that if the gesture is a fist, the client logic can perform the task of selecting an electrode, and if the gesture is an upward hand motion, the client logic can perform the task of increasing the temperature of the selected electrode.

To operate the inventive system, the user must first gain control and activate touch free operation. To gain control, the user makes the system acknowledge that the user will be sending instructions. The system then responds to the instructions which are, as discussed above, in the form of different hand gestures and/or head and/or other body movements. Control can be released when it is no longer needed or after a period of motionlessness is detected. Gaining control can be achieved by either using a focusing gesture, for example, a hand wave or head movement, or by use of hardware, such as a foot pedal that enables control while pressed, or by a voice command.

The motions detected by the system do not have fixed functions. The system associates meaning to each gesture, pose or movement depending on its context according to the function and mode in which the user is currently operating the client computer 16. For example, while the user is operating the client in selection mode, a head movement may change the mode from unipolar to bipolar and vice versa.

During the time that the touch free control is activated, a visual indication can be shown to the user. Optionally, an audible indication may be given upon activation and deactivation of the touch free control.

In one embodiment, the hands free operation can be augmented with voice input which could be used separately or in conjunction with detected motions. Microsoft® Kinect, for example, has peripheral microphones and can detect the direction from which the voice recognized came. This and/or other voice recognition techniques can be used to capture voice commands and selectively filter the voice commands from the user. The voice commands can be combined with the gestures. For example, the user could say "Ablator Power" and then move his hand up and down to control the power. In another example, the user could say "Ablator Temperature" and then move his hand up and down to control the temperature setting. Yet another example could be the user saying "Ablator Electrodes", and the motion of the hand left and right would highlight the electrode controls on the screen and a "press forward" will toggle the selection. In another example, the user could say "Ablator Electrodes None/Even/Odd/All" will select or deselect electrodes appropriately. The client computer performs all the logic in deciding what each motion means in conjunction with the most recently recognized voice command. In one version of this embodiment, some commands may be performed by the use of voice commands only or gestures only e.g., setting the ablation mode can be performed just by saying "Ablator Bipolar" or "Ablator Unipolar" without the need for a gesture.

Figure 2:
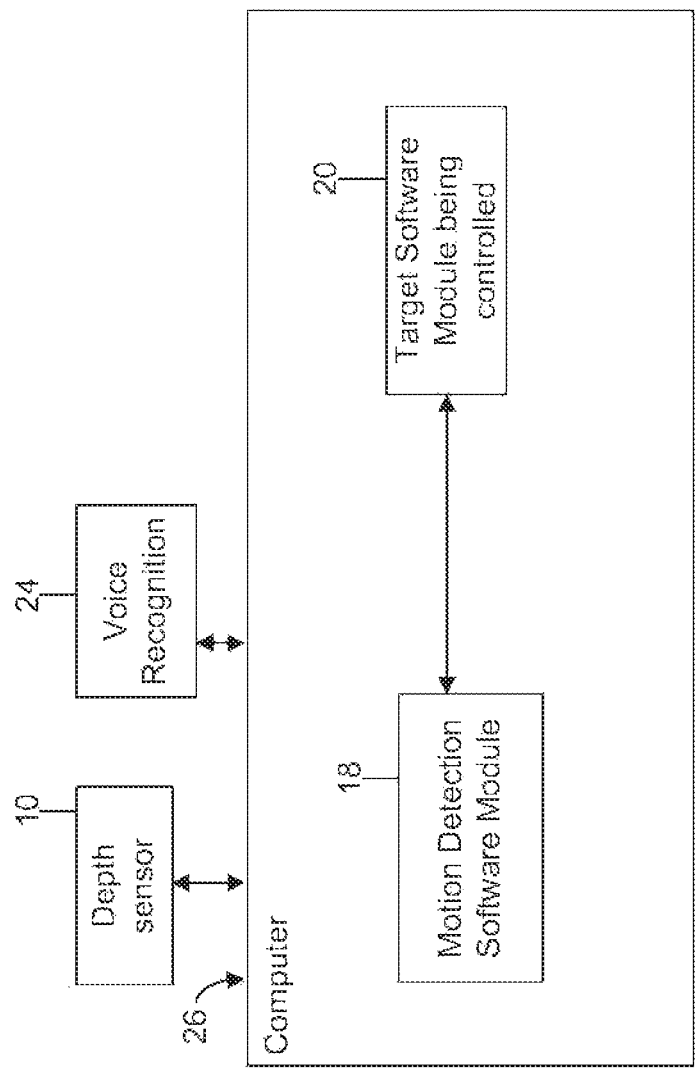
FIG. 2 is a block diagram of another embodiment of the inventive system.

FIG. 2 shows an embodiment having modules of both the CPU and the client computer in one workstation 26. The system in the embodiment shown in FIG. 2 has the Depth Sensor 10, Voice Recognition 24, Motion Detection Software Module 18 and Target Software Module 20, having the same functionality as those components in FIG. 1. In this embodiment, however, only one workstation 26 is used and the Target Software Module 20 contains a client communication module. The invention is not limited to either the configuration of FIG. 1 or FIG. 2. Multiple CPUs, each having one or more modules, can also be used.

Figure 3:
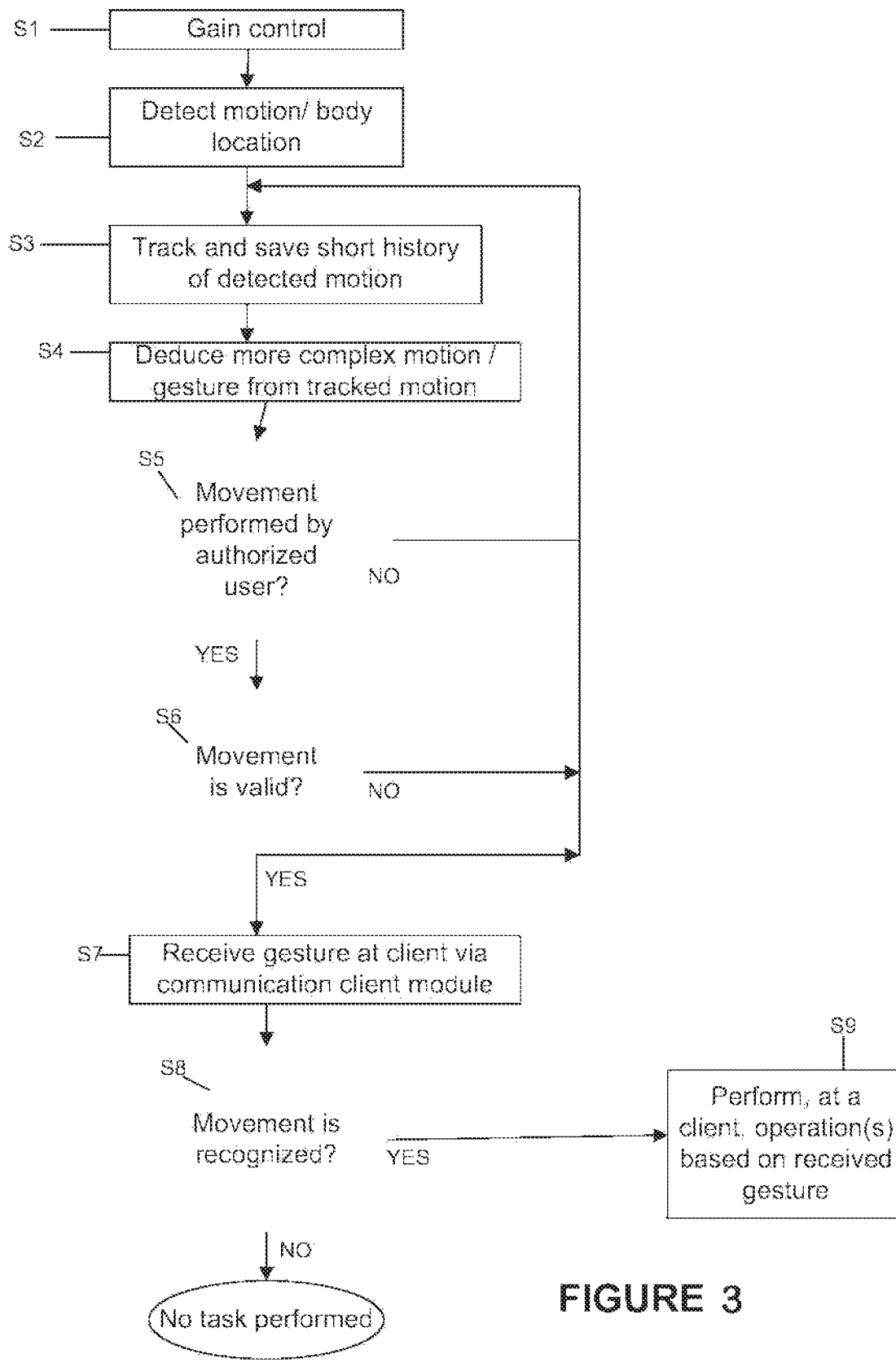
FIG. 3 is a flow diagram of the inventive method.

FIG. 3 is a flow diagram of the inventive method. In step SI, the user gains control of the touch free control system, typically by performing a motion, a voice command or pressing a foot pedal. In step S2, movement, including change of location, is detected by the depth sensor 10 and transmitted to the CPU 12. In step S3, the CPU tracks and saves a short history of the movements and/or location changes. In step S4, the CPU 12 uses the motion software to deduce, from the received motion in accordance with the short history, a more complex movement or gesture. In steps S5 and S6, filtering is performed. In step S5, it is determined whether the gesture is performed by the authorized or proper user by determining whether the movement is within a predicted location and/or by performing facial recognition. If the gesture is determined to be by the authorized user (S5=YES), then processing continues at step S6 where the gesture is validated by the CPU. If the gesture is valid (S6=YES), then it is sent to the client computer and additional motion tracking is resumed at step S3. At step S7, the gesture is received at the communication client module on the client computer. If the gesture is recognized by the active Target Software Module (S8=YES), then, at step S9, the client computer performs a device function or operation, e.g., task, at the ablator workstation in accordance with the client logic or Target Software Module, based on the deduced gesture. These tasks include, but are not limited to, changing the power settings of one or more electrodes, changing the maximum allowed temperature for one or more electrodes, changing the ablator mode (unipolar or bipolar), selecting and deselecting electrodes for ablator, etc. Once the motion software sends the gesture to the client computer (when S6=YES), the motion software goes back to responding to the next detected motion and/or body location.

In one embodiment, performing an authorized movement also requires determining if the movement is performed in conjunction with hardware such as another device. In this embodiment, an authorized movement must include both a complex movement deduced by the software and an additional action, such as stepping on a foot pedal. This authorization can be performed after step S5, when S5=YES, and before step S6.

If the detected movement is not authorized (S5=NO) or the detected movement is not valid (S6=NO), processing continues at step S3. If the gesture is not recognized by the client software (S8=NO), then no task is performed.

The inventive system advantageously enables tasks to be performed by an operating room device using head tracking and/or other motion detection techniques allowing the doctor or other system user to perform certain actions while still using at least one of his hands for catheter navigation. Beneficially, the system can filter and forward gestures for allowed personnel only. This ensures that the system is only controlled by the intended people. Hand gestures and head movements and other actions by other people can be ignored.

Various aspects of the present disclosure may be embodied as a program, software, or computer instructions embodied or stored in a computer or machine usable or readable medium, which causes the computer or machine to perform the steps of the method when executed on the computer, processor, and/or machine. A program storage device readable by a machine, e.g., a computer readable medium, tangibly embodying a program of instructions executable by the machine to perform various functionalities and methods described in the present disclosure is also provided.

The system and method of the present disclosure may be implemented and run on a general-purpose computer or special-purpose computer system. The computer system may be any type of known or will be known systems and may typically include a processor, memory device, a storage device, input/output devices, internal buses, and/or a communications interface for communicating with other computer systems in conjunction with communication hardware and software, etc. The system also may be implemented on a virtual computer system, colloquially known as a cloud.

The computer readable medium is a computer readable storage device, which may be, for example, a magnetic, optical, electronic, electromagnetic, infrared, or semiconductor system, apparatus, or device, or any suitable combination of the foregoing; however, the computer readable storage device is not limited to these examples. Additional particular examples of the computer readable storage device can include: a portable computer diskette, a hard disk, a magnetic storage device, a portable compact disc read-only memory (CD-ROM), a random access memory (RAM), a read-only memory (ROM), an erasable programmable read-only memory (EPROM or Flash memory), an electrical connection having one or more wires, an optical fiber, an optical storage device, or any appropriate combination of the foregoing; however, the computer readable storage medium is also not limited to these examples. Any tangible medium that can contain, or store a program for use by or in connection with an instruction execution system, apparatus, or device could be a computer readable storage device.

The terms "computer system" and "computer network" as may be used in the present application may include a variety of combinations of fixed and/or portable computer hardware, software, peripherals, and storage devices. The computer system may include a plurality of individual components that are networked or otherwise linked to perform collaboratively, or may include one or more stand-alone components. The hardware and software components of the computer system of the present application may include and may be included within fixed and portable devices such as desktop, laptop, and/or server, and network of servers (cloud). A module may be a component of a device, software, program, or system that implements some "functionality", which can be embodied as software, hardware, firmware, electronic circuitry, or etc.

The embodiments described above are illustrative examples and it should not be construed that the present invention is limited to these particular embodiments. Thus, various changes and modifications may be effected by one skilled in the art without departing from the spirit or scope of the invention as defined in the appended claims.

What is claimed is:

1. A system for touch-free operation of an ablator workstation by an associated user, comprising:
   a depth sensor configured to detect location of the associated user;
   a hardware device configured to receive input from the associated user; and
   a processor with a memory device, wherein the memory device is configured to store instructions that, when executed by the processor, cause the processor to:
      predict a subsequent location of the user based on an initial location of the user,
      detect the subsequent location of the user to determine if the subsequent location of the user is within the predicted location of the user,
      receive a hardware device input, wherein the hardware device input occurs at the subsequent location of the user, and
      identify the hardware device input as being unauthorized when the subsequent location of the user is beyond the predicted location of the user,
   wherein the task is one of changing power settings of an electrode, changing maximum allowed temperature for the electrode, changing ablation mode, electrode selection for ablation, and electrode deselection for ablation.

2. The system of claim 1, wherein the hardware device input occurs at a predetermined time during a procedure.

3. The system of claim 1, wherein the ablator workstation is disassociated from the associated user after a period of motionlessness.

4. The system of claim 1, wherein association of the ablator workstation to the user gives the user control of the ablator workstation.

5. The system of claim 1, wherein the hardware device input is authorized based on facial recognition detected by the depth sensor.

6. The system of claim 1, wherein a different ablator task is caused to be performed when a different gesture is detected in conjunction with the hardware device input.

7. The system of claim 1, wherein the ablator task performed by the ablator workstation is identified based on a state of the processor.

8. The system of claim 1, wherein the detected location of the associated user is saved in a history.

9. A system for touch-free operation of an ablator workstation by an associated user, comprising:
   a depth sensor configured to detect location of the associated user;
   a hardware device configured to receive input from the associated user; and
   a processor with a memory device, wherein the memory device is configured to store instructions that, when executed by the processor, cause the processor to:
      predict a subsequent location of the user based on an initial location of the user,
      detect the subsequent location of the user to determine if the subsequent location of the user is within the predicted location of the user,
      receive a hardware device input, wherein the hardware device input occurs at the subsequent location of the user,
      authorize the hardware device input when the subsequent location of the user is within the predicted location of the user, and
      cause the ablator workstation to perform an ablator task after the hardware device input is authorized,
   wherein the task is one of changing power settings of an electrode, changing maximum allowed temperature for the electrode, changing ablation mode, electrode selection for ablation, and electrode deselection for ablation.

10. The system of claim 9, wherein the hardware device input occurs at a predetermined time during a procedure.

11. The system of claim 9, wherein the ablator workstation is disassociated from the associated user after a period of motionlessness.

12. The system of claim 9, wherein association of the ablator workstation to the user gives the user control of the ablator workstation.

13. The system of claim 9, wherein the hardware device input is authorized based on facial recognition detected by the depth sensor.

14. The system of claim 9, wherein a different ablator task is caused to be performed when a different gesture is detected in conjunction with the hardware device input.

15. The system of claim 9, wherein the ablator task performed by the ablator workstation is identified based on a state of the processor.

16. The system of claim 9, wherein the detected location of the associated user is saved in a history.

* * * * *